United States Patent
Yoo et al.

(10) Patent No.: US 8,131,662 B2
(45) Date of Patent: Mar. 6, 2012

(54) REMOTE VISION TESTING DATA COLLECTION

(75) Inventors: Herb Yoo, Beaverton, OR (US); Alan W. Reichow, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 740 days.

(21) Appl. No.: 12/239,709

(22) Filed: Sep. 26, 2008

(65) Prior Publication Data

US 2009/0192361 A1     Jul. 30, 2009

Related U.S. Application Data

(60) Provisional application No. 60/975,400, filed on Sep. 26, 2007.

(51) Int. Cl.
*G06N 5/00* (2006.01)

(52) U.S. Cl. .......................... 706/54; 706/45

(58) Field of Classification Search .................. 706/54, 706/45

See application file for complete search history.

(56) References Cited

OTHER PUBLICATIONS

Ciorba, Neonatal newborn hearing screening: four years' experience at Ferrara University Hospital (CHEAP Project): Part 1, ACTA Otorhinolaryngologica Italica, 2007, v.27, pp. 10-16.*

* cited by examiner

*Primary Examiner* — Wilbert L Starks

(74) *Attorney, Agent, or Firm* — Shook, Hardy & Bacon L.L.P.

(57) ABSTRACT

This invention is related to systems and methods of providing sensory ability data from one or more remote locations to a central location. One embodiment of the present invention includes a method comprising the steps of testing the sensory ability of a subject to produce testing data thereof, the testing being administered at one or more remote locations; collecting the testing data in an electronic format; and electronically providing the formatted testing data to the central location from the remote location. After being transferred, the testing data may be analyzed at the central location, and a sensory training plan may be developed for the individual. Further embodiments may automatically collect the testing data, transfer the data from the remote location to the central location, and/or analyze the data at the central location.

8 Claims, 6 Drawing Sheets

600

602 — Demographics:
- Athlete #:
- Name: First / Last
- Gender:
- Date of Birth:
- Date of Evaluation:
- Time of Evaluation:
- Evaluation Level:
- Primary:
- Secondary:
- Third:
- Sport | Years | Position | Position

626

604 — Static Visual Acuity: OD 20/ | OS 20/ | OU 20/

606 — Dominance:
| Eye | Comment |
| Hand | |
| Foot | |

608 — NPC: OU | OD NLOS | OS NLOS

610 — Contrast Sensitivity:

| OU | OD | OS |
|---|---|---|
| A | A | A |
| B | B | B |
| C | C | C |
| D | D | D |

628

612 — Depth Perception:

| | Primary | Right Field Gaze | Left Field Gaze |
|---|---|---|---|
| 240" | | | |
| 120" | | | |
| 60" | | | |
| 30" | | | |

614 — Eye-Hand Coordination:
| Self-paced | |
| Instrument paced | |

616 — Split Attention:
| Test 1 | | |
| Test 2 | | |
| Test 3 | | |

618 — Eye-Body Coordination: E-9-27-E

628

620 — Acc/Verge Facilities

| | OU | | OD | | OS | |
|---|---|---|---|---|---|---|
| | 1st 30 | 2nd 30 | 1st 30 | 2nd 30 | 1st 30 | 2nd 30 |
| Acc. Facility | | | | | | |
| Verge Facility | | | | | | |
| | Called | Errors | Called | Errors | Called | Errors |
| AVF | | | | | | |
| AVF | | | | | | |

622 — Reaction Plus: Reaction | Motor Response | Overall Response

Vision and Balance: Static Eyes Open | Eyes Closed

Static eye movements OU | OD | OS

Dynamic Eyes Open | Eyes Closed

624 — DVT:
Perception time | Target Following
Target Acquisition | Gaze Stabilization

*FIG. 6.*

REMOTE VISION TESTING DATA COLLECTION

This application claims the benefit of priority of U.S. Provisional Patent Application 60/975,400, filed Sep. 26, 2007, which is incorporated by reference in its entirety herein.

TECHNICAL FIELD

The present invention relates generally to the testing and training of the sensory abilities of individuals. More particularly, the present invention relates to the remote testing of an individual's sensory ability.

BACKGROUND

One skilled in the art of sensory evaluation will be aware of a large number of sensory tests that may be performed to determine strengths and weaknesses of an individual's sensory abilities. Typically, such tests are applied to determine whether an individual may benefit from some form of sensory correction and/or training and, if so, what type and degree of sensory correction and/or training may be desirable. One skilled in the art will further realize that numerous activities, particularly competitive athletics, place particularized demands upon the sensory abilities of an individual.

SUMMARY

The present invention provides systems and methods of testing a subject's sensory ability at a remote location and analyzing the resulting sensory testing data at a central location. More particularly, a method in accordance with the present invention may provide sensory ability data from one or more remote locations to a central location. The method may comprise testing the sensory ability of a subject to create testing data at a remote location, collecting the testing data in an electronic format, providing the formatted testing data to a central location from the remote location, analyzing the testing data and formulating a sensory training program at the central location, and transmitting the analysis and/or training program to the remote location.

A system in accordance with the present invention may comprise a testing device to test a subject's sensory ability, where the testing occurs at a remote location and provides testing data; a computing device with the testing data, where the testing data is collected by a test administrator at a remote location; and a data transfer device to transfer the testing data from the remote location to a central location.

It should be noted that this Summary is provided to generally introduce the reader to one or more select concepts described below in the Detailed Description in a simplified form. This Summary is not intended to identify key and/or required features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein:

FIG. 6 illustrates a spreadsheet in accordance with an embodiment of the present invention.

DETAILED DESCRIPTION

Figure 1:
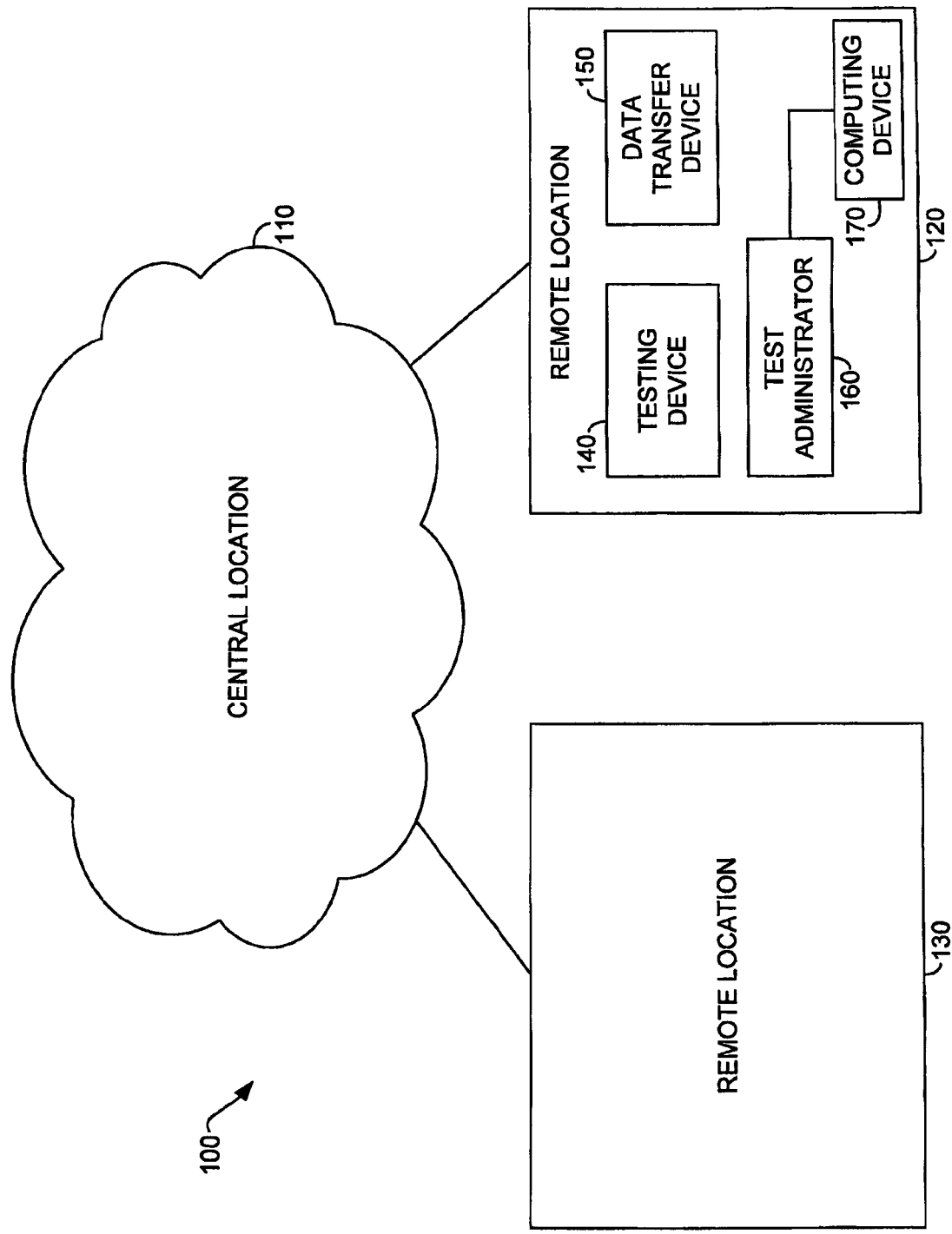
FIG. 1 illustrates a system in accordance with embodiments of the present invention.

The present invention allows testing and data collection to occur at a remote location different from the location where the analysis or assessment is performed and the training plan is developed. In accordance with this invention, sensory ability testing may occur at one or more remote locations, while the analysis of the testing data and development of the training plan occurs at a central location. The central location may analyze the data, and further may have the capability to access a network, such as the Internet, in order to receive data from the one or more remote locations. A remote location is any location other than the central location, where testing may occur (e.g., a college athlete might undergo testing at their college's athletic facilities), and includes the capability to perform sensory ability testing and to access a network in order to transfer testing data to the central location.

Sensory testing gathers data on a subject's current sensory ability. Sensory ability may refer to a subject's sensory ability, perceptual ability, cognitive ability, visual ability, auditory ability, etc. The specific tests administered to a subject will vary depending on the individual's ability, desired activity, and competitive level. Using such tests, it may be determined during the assessment that the individual has a particular weakness and/or strength in a different aspect of his sensory ability. Given this weakness, a training program may be created to train the individual on that weakness. For example, if an individual's saccadic and peripheral sensory ability is weak, various baseline measurements will be analyzed during the assessment to determine such a weakness. Or, if, after testing and assessing, it is determined that an individual has focusing problems at specific gaze angles, dynamic tracking ability may be trained.

An individual's particularized activity may play a role in the specific tests administered. For example, an individual that participates in baseball will likely utilize different sensory skills than a soccer player, and therefore those two individuals will benefit from different sensory training plans and thus may undergo different sensory tests, although certain core tests might be used in each.

Additionally, the competitive level of the individual may lead to alterations in testing and training plans, so individuals may be assigned a specific evaluation level prior to testing. For instance, if the desired activity is some type of sport, a high school athlete may be tested using a different evaluation level and thus receive a different training program than a college-level athlete, and a college-level athlete may be tested using a different evaluation level than a professional level athlete. Typically, the higher the elevation level of the individual the more tests they may undergo.

Generally, the data collected from each subject may include demographic information, static sensory data, dynamic sensory data, and, optionally, health data. Demographic information may include the individual's name, gender, primary activity, evaluation level, and the like. Static sensory data may include, for example, measurements of the individual's standard vision, static visual acuity, contrast sensitivity, depth perception, etc. Dynamic sensory data may include eye-hand coordination, dynamic visual acuity, split attention, eye-body coordination, dynamic tracking, etc.

Examples of health data may include the dates of the previous examinations, gender, weight, etc. Once the testing has occurred, the data may be reviewed (e.g., by the trainer administering the testing) to verify the data prior to transferring the data to a central location. That is, the data may receive an initial check for obvious errors in case more testing is required.

Once the data is acquired from testing, it may then be collected. One skilled in the art with appreciate that the testing data may be collected using various methods. By way of example, but not limitation, data may be collected in an electronic format by entering the data into a spreadsheet. Collection may occur indirectly, where an individual (e.g., a trainer) inputs the data using an input device, or directly, where the testing device automatically puts the data into a format to transfer the data. In another embodiment, the data may be collected by entering the testing data on a web portal that resides on a network. Again, in embodiments using a web portal, the data may be collected or entered directly or indirectly. One skilled in the art will appreciate that any type of computing device may be used in connection with one or more embodiments of the present invention. Exemplary computing devices include hand-held devices, consumer electronics, general-purpose computers, specialty-computing devices, and the like.

After the data has been collected, the data may be transferred to a central location for analysis. One skilled in the art will appreciate that various methods may be utilized to transfer the testing data to a central location. For example, the data may be collected in an electronic format, and thus the transfer of data may occur electronically. If, for example, the data has been collected on a spreadsheet, the spreadsheet containing the testing data may be transferred via email over the network to the central location. Alternatively, where the data has been collected in a web portal, the central location may access the web portal to retrieve the testing data.

The present invention may also provide for automatic collection and/or automatic transfer of testing data from one or more remote locations to a central location. In these embodiments, the various testing devices may have the capability to collect and/or transfer the testing data. Examples of such testing devices include eye movement monitors, touch screens, display devices, input devices, corneal analyzers, etc. Thus, the device may measure an aspect of the individual's sensory ability and automatically collect the testing data in specified format. Further, the testing devices may have the capability of directly connecting to a network, which would allow the device to measure the data during the sensory ability tests, and automatically send the data to the central location to be analyzed, rather than first collecting the data before sending it to a central location.

Once the sensory ability data of an individual has been transferred to a central location, this data may be analyzed. Analysis of this data may be used to create a specific sensory ability training plan for the subject. Such analysis may occur manually by an administrator at the central location who might receive the testing data, interpret the data, and create a training plan based on their personal expertise. Alternatively, analysis may occur automatically. That is, the process may be automated where the data may be analyzed by, for example, a computing device.

Turning now to the figures, FIG. 1 illustrates a sensory testing system 100 in accordance with an embodiment of the present invention. System 100 may include a central location 110 and one or more remote locations, such as a first remote location 120 and a second remote location 130. As described above, testing of a subject's sensory ability occurs at first remote location 120. Each remote location may comprise various components, although each remote location does not necessarily comprise the same components. It will be understood and appreciated by those of ordinary skill in the art that each remote location shown in FIG. 1 is merely an example of one suitable remote location and is not intended to suggest any limitation as to the scope of use or functionality of the present invention. Neither should the remote location 120 be interpreted as having any dependency or requirement related to any single component or combination of components illustrated therein. As can be seen in the embodiment illustrated in FIG. 1, remote location 120 has a testing device 140, a data transfer device 150, a test administrator 160, and a computing device 170.

The testing device 140 may include any device capable of testing or measuring sensory ability. The test administrator 160 may collect the testing data provided by the testing device 140 in an electronic format and may store the collected testing data to a computing device 170. Once this occurs, the data transfer device 160 may transfer the testing data, via any suitable method depending on the format of the data, to the central location 110. The data transfer device 160 may be any device that can transfer data, such as a modem, network card, and the like.

Figure 2:
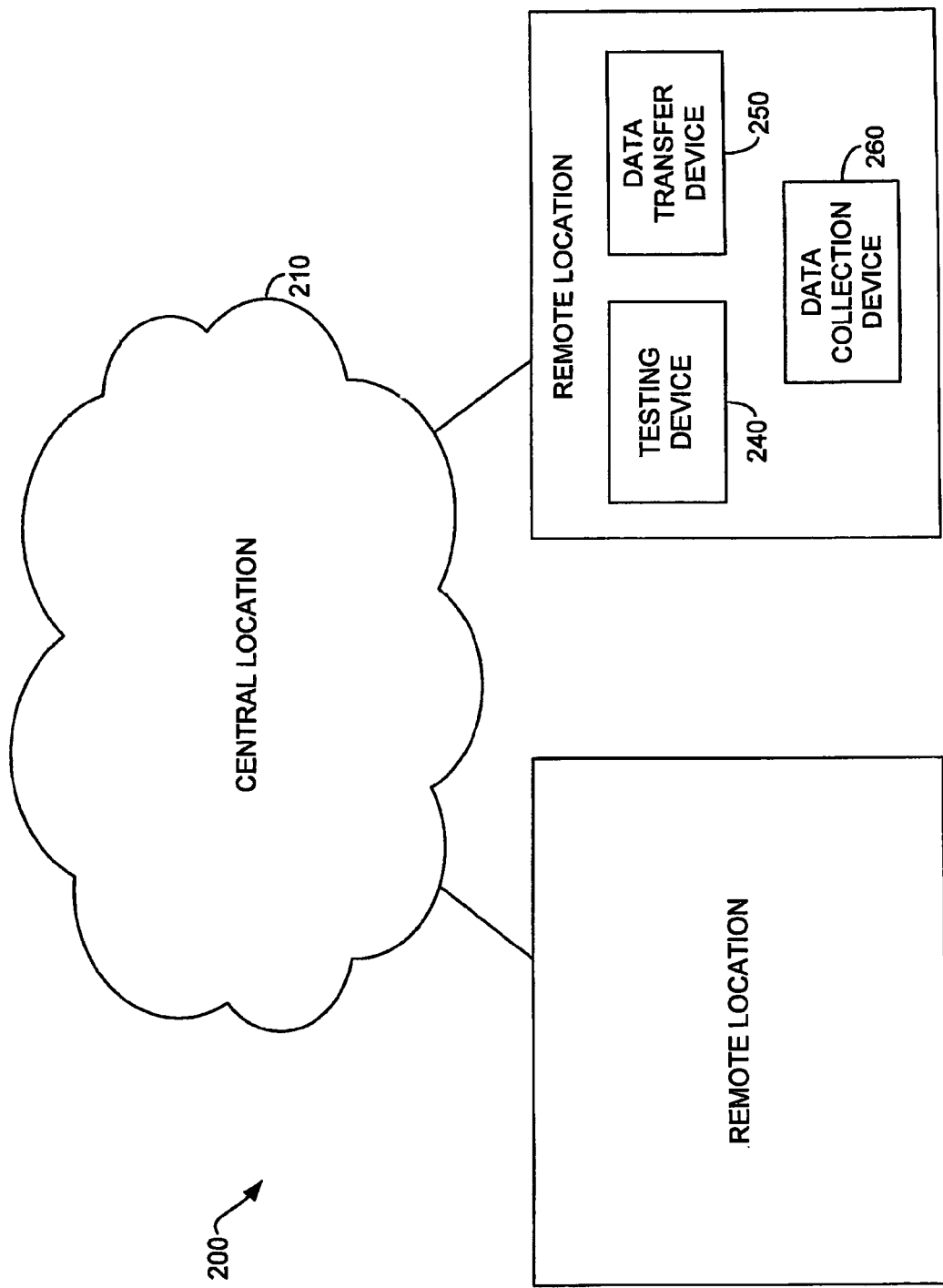
FIG. 2 illustrates a further system in accordance with embodiments of the present invention.

Referring now to FIG. 2, this figure illustrates a further sensory testing system 200 in accordance with an embodiment of the present invention. System 200 may include a central location 210 and one or more remote locations, such as a first remote location 220 and a second remote location 230. As described above, testing of a subject's sensory ability may occur at first remote location 220. In FIG. 2, remote location 220 has a testing device 240, a data transfer device 250, and a data collection device 260. The testing device 240 may create the data resulting from the sensory ability tests administered to a subject or any other sensory ability measurements. In this embodiment, the data collection device 260 may collect the data provided by testing device 240. By way of example, and not limitation, data collection device 260 may be any device which includes solid-state memory, hard drives, flash memory, and the like. Further, as discussed above, the data collection device 260 may collect the data from the testing device 240, either directly or indirectly. That is, an individual may directly input data from the testing device 240 into the data collection device 260. Or, the devices may work together to directly collect the data.

Figure 3:
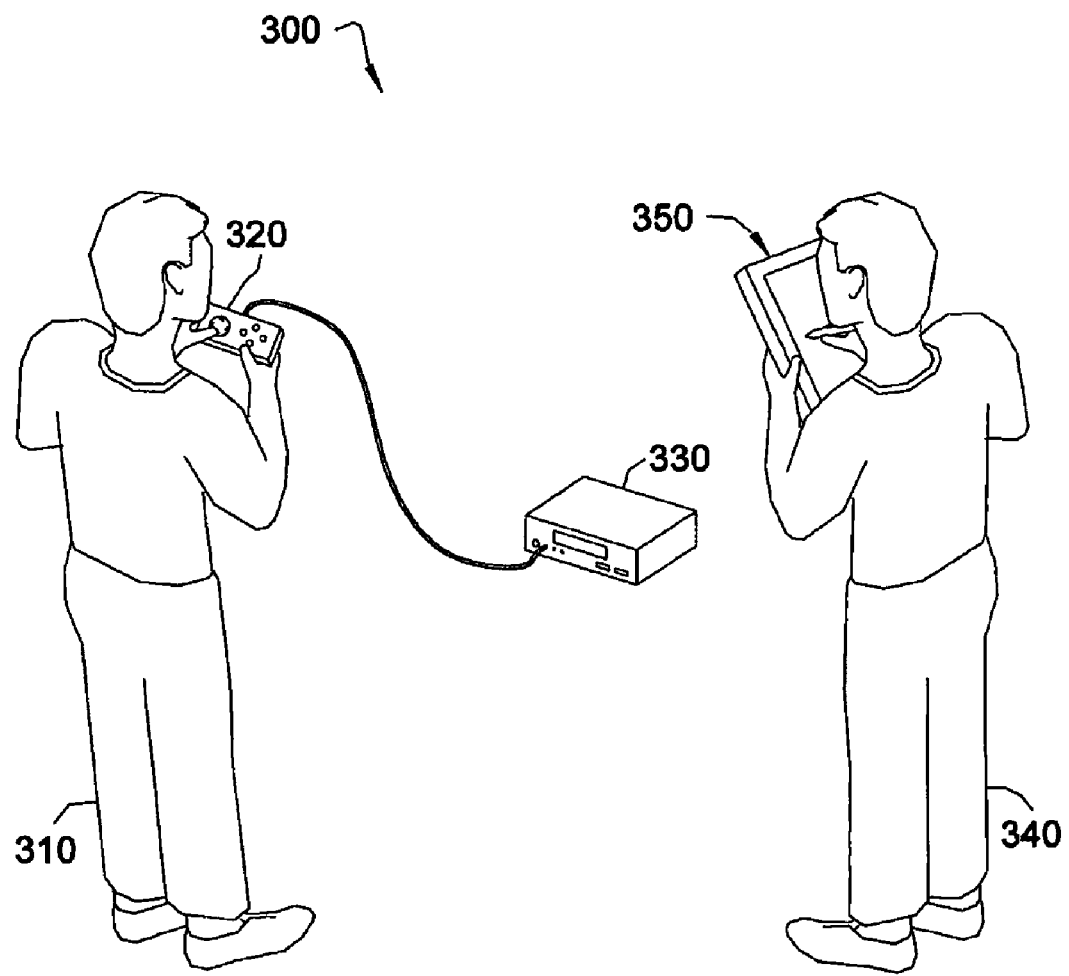
FIG. 3 illustrates a further system in accordance with embodiments of the present invention.

Referring now to FIG. 3, a system 300 in accordance with embodiments of the present invention is illustrated. Test subject 310 may use system 300 to test the sensory ability of subject 310 using an input device 320, such as a keyboard, joystick, touchscreen device, and the like. System 300 may also include a testing unit 330. One skilled in the art will further appreciate that input device 320 may comprise multiple devices, that in combination, provide some of the sensory ability testing for a particular activity. In this embodiment, after the subject 310 has completed the testing, a tester 340 may collect the resulting data by entering the testing data into a computing device 350. As described above, any computing device capable of collecting data may be used by tester 340.

Figure 4:
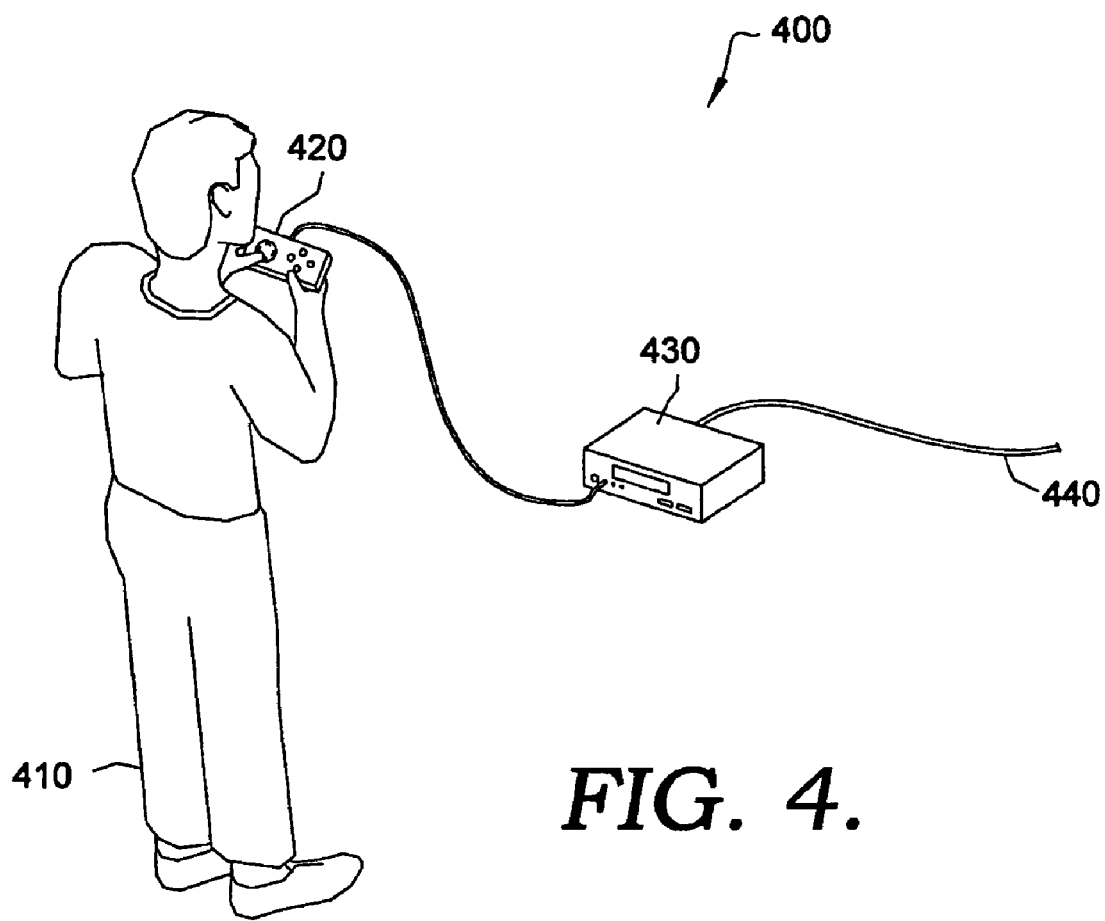
FIG. 4 illustrates a further system in accordance with embodiments of the present invention.

Referring now to FIG. 4, an additional system 400 is illustrated. System 400 shows an embodiment similar to FIG. 3 in that system 400 includes a subject 410, a testing device 420, and an input device 430. However, in this embodiment, the input device 430 is also connected, via connection 440, to a network. Further, connection 440 may be wired or wireless. Using connection 440 to connect input device 430 to a network allows the testing data to be directly transferred from the remote location to a central location, as described above.

Figure 5:
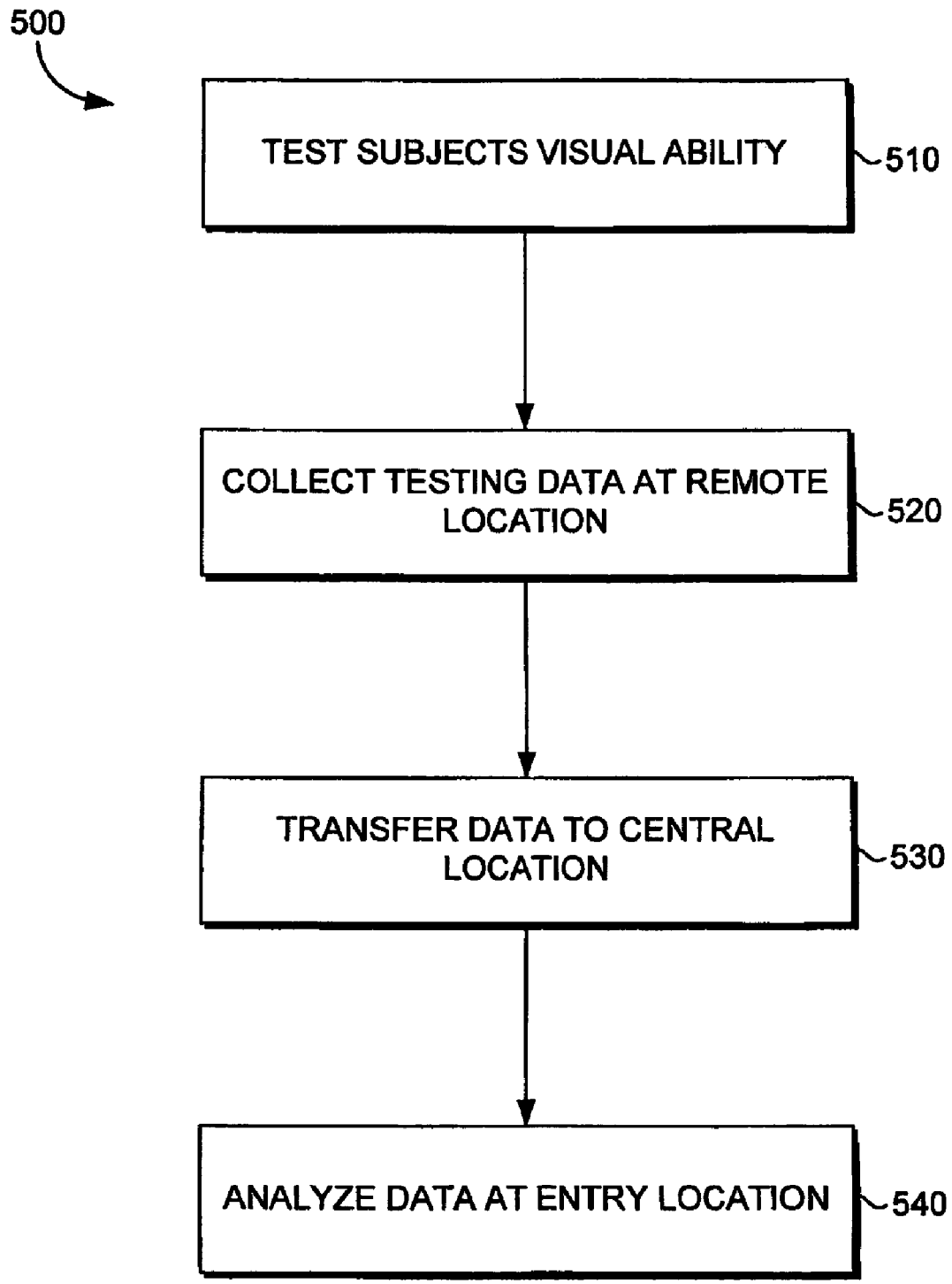
FIG. 5 illustrates a method in accordance with embodiments of the present invention.

Referring now to FIG. 5, a method 500 in accordance with embodiments of the present invention is illustrated. In step 510, testing of the subject at a remote location may occur. Step 510 may utilize any type of testing device. As described above, the testing in step 510 may vary between subjects based on their desired activity and on their level of ability or competition. In step 520, the data resulting from the testing of step 510 may be collected in an electronic format. For example, as described above, the data may be collected in a spreadsheet. More particularly, the format of the data may depend upon how the data will be transferred. Such a transfer of the data occurs in step 530. At this step, the testing data may be transferred from the remote location where the testing occurred to a central location where the analysis may occur. By way of example, without limitation, if the data was collected electronically on a spreadsheet, the spreadsheet could be send by email to the central location. In step 540, the central location may analyze the data received from the remote location in order to develop an appropriate sensory training plan for the individual. One skilled in the art will appreciate that the present invention permits the period of time between steps 510 and 540 to be relatively short, which allows for the individual to receive a training plan sooner and thus begin training sooner. For example, the entire process may occur quickly enough that the individual receives the training plan while still at the testing location.

Referring now to FIG. 6, a spreadsheet 600 in accordance with embodiments of the present invention is illustrated. The spreadsheet 600 provides an example of testing data collected (e.g., as in step 520 in FIG. 5) and includes various data fields. One skilled in the art will appreciate that these data fields may be altered as necessary for the individual subject. Preferably, spreadsheet 600 may be used in the testing of an individual participating in a sporting activity. At 602, in spreadsheet 600, various demographic information may be entered. At 626 the primary, secondary, etc. sport of the subject may be entered. Next, data measuring the subject's static visual acuity 604, eye dominance 606, NPC 608, and contrast sensitivity 610 may be entered. The depth perception of the subject can be measured and entered into the spreadsheet 600 at 612. These measurements may be performed at multiple distances to determine the primary depth perception of the subject. Further, data fields may be included for more advanced testing depending on the subject's evaluation level as can be seen at 628.

Next, the dynamic visual acuity of the subject may be measured and entered in data fields 614-624. These data fields may include eye-hand coordination 614, split attention 616, eye-body coordination 618, acc/verge facilities 620, reaction 622, and dynamic visual tunnel 624. Once again, the spreadsheet 600 may be configured to allow for more advanced measurements of acc/verge facilities based upon the subject's evaluation level at 628. Thus, a subject at a college or professional evaluation level may perform additional tests, the measurements of which will be entered at 628.

The present invention has been described herein in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain the ends and objects set forth above, together with other advantages which are obvious and inherent to the methods. It will be understood that certain features and sub-combinations are of utility and may be employed without reference to other features and sub-combinations. This is contemplated by and within the scope of the claims.

The invention claimed is:

1. A method of developing a sensory training program for a subject using testing data from a remote location, the method comprising:
    testing the subject's sensory ability at a remote location to produce testing data thereof;
    collecting the testing data in an electronic format at the remote location;
    providing the formatted testing data to a central location;
    analyzing the testing data at the central location to create an assessment of the subject's sensory ability;
    developing a sensory training program for the subject at the central location using the assessment; and
    transmitting the program to the remote location.

2. The method of claim 1, further comprising assigning an evaluation level to the subject.

3. The method of claim 2, wherein testing the sensory ability of the subject is based on the assigned evaluation level of the subject.

4. The method of claim 1, wherein the testing data includes demographic information.

5. The method of claim 1, wherein the testing data includes static sensory data.

6. The method of claim 1, wherein the testing data includes dynamic sensory data.

7. The method of claim 1, wherein the testing data includes health data.

8. The method of claim 1, wherein the step of collecting the testing data is performed automatically by a data collection device.

* * * * *